| United States Patent [19] | [11] | 4,182,731 |
|---|---|---|
| Schulz et al. | [45] | Jan. 8, 1980 |

[54] PREPARATION OF AQUEOUS SOLUTIONS OR FINE AQUEOUS DISPERSIONS OF POLYENYLTRIARYLPHOSPHONIUM SALTS

[75] Inventors: Bernhard Schulz, Schwetzingen; Paul Grafen, Weisenheim; Hans-Ulrich Scholz, Lampertheim; Hans Grassner, Heidelberg; Werner Reif, Frankenthal, all of Fed. Rep. of Germany

[73] Assignee: BASF Aktiengesellschaft, Fed. Rep. of Germany

[21] Appl. No.: 912,356

[22] Filed: Jun. 5, 1978

[30] Foreign Application Priority Data

Jun. 18, 1977 [DE] Fed. Rep. of Germany ....... 2727384
Jul. 2, 1977 [DE] Fed. Rep. of Germany ....... 2729974

[51] Int. Cl.$^2$ .............................................. C07F 9/54
[52] U.S. Cl. ............................... 260/606.5 F; 252/182
[58] Field of Search ................. 260/606.5 F; 560/607, 560/608, 609

[56] References Cited

U.S. PATENT DOCUMENTS

| 2,905,717 | 9/1959 | Sarnecki et al. | 260/606.5 F |
|---|---|---|---|
| 2,945,069 | 7/1960 | Stern | 260/606.5 F |
| 2,950,321 | 8/1960 | Sarnecki et al. | 260/606.5 F |
| 3,294,844 | 12/1966 | Sarnecki et al. | 260/606.5 F |
| 3,347,932 | 10/1967 | Chechak | 260/606.5 F |
| 3,373,207 | 3/1968 | Nuerrenbach et al. | 260/606.5 F |
| 3,408,414 | 10/1968 | Surmatis | 260/606.5 F |

Primary Examiner—Helen M. S. Sneed
Attorney, Agent, or Firm—Keil & Witherspoon

[57] ABSTRACT

Aqueous solutions of polyenyltriarylphosphonium salts are prepared from solutions of the corresponding polyenyltriarylphosphonium salts in organic solvents by driving off the solvent with steam, part of the steam being allowed to condense. Some of the said triarylphosphonium salts may be used directly as pesticides while others are used as intermediates for organic syntheses, especially in the carotinoid field.

4 Claims, No Drawings

PREPARATION OF AQUEOUS SOLUTIONS OR FINE AQUEOUS DISPERSIONS OF POLYENYLTRIARYLPHOSPHONIUM SALTS

The present invention relates to a process for the preparation of an aqueous solution or aqueous fine dispersion of a polyenyltriarylphosphonium salt of the general formula I $$[R-P(Ar)_3]^{\oplus} X^{\ominus} \qquad \text{I}$$

where R is an aliphatic, cycloaliphatic-aliphatic or aromatic-aliphatic polyenyl radical of 5 to 20 carbon atoms, X is the anion equivalent of a strong acid and Ar is aryl, especially phenyl.

Some of the compounds I (for example where R in I is β-ionylidene-ethyl) may be used directly as pesticides, for example for combating water snails, whilst others serve as intermediates for organic syntheses, especially in the carotinoid field (cf., inter alia, German Patent Nos. 1,203,264 and 1,046,046). Both for direct application, and for further syntheses, for example for the manufacture of symmetrical carotinoids as described in German Laid-Open Application DOS No. 2,505,869, it is frequently advantageous to use an aqueous solution or an aqueous fine dispersion of the compounds I.

According to Houben-Weyl, "Methoden der Organischen Chemie", volume XII/1, pages 90 et seq., phosphonium salts are obtained from triphenylphosphine, an acid and an alcohol in accordance with the equation $$(C_6H_5)_3P + HX + HOR \rightarrow [(C_6H_5)_3\overset{+}{P}-R]X^- + H_2O$$

Solvents which have been disclosed for this reaction are lower aliphatic alcohols, lower carboxylic acids, eg. HCOOH or CH₃COOH, acetone and the conventional water-insoluble solvents, eg. benzene, toluene, tetrahydrofuran, acetonitrile, methylene chloride, chloroform, diethyl ether, dioxane and esters, eg. methyl acetate and ethyl acetate; this means that the conventional methods of manufacture give a solution of I in one of the above solvents. The direct reaction of triphenylphosphine with an acid and a polyene-alcohol in water, in order to prepare an aqueous solution of a polyenyltriphenylphosphonium salt (I), appears a hopeless approach, since on the one hand neither the triphenylphosphine nor the polyene-alcohol is water-soluble, whilst on the other hand compound I must be expected to be very sensitive to hydrolysis at elevated temperatures, and it can be assumed that the presence of substantial amounts of one of the products formed during the desired reaction would have an adverse effect on the reaction equilibrium.

Using the conventional process, the best yields of I are obtained when using a lower alcohol, eg. ethanol, isopropanol, isobutanol, n-propanol, n-butanol and especially methanol as the solvent. Accordingly, the preferred starting solutions for the preparation of an aqueous solution of I are solutions of I in the above lower alcohols, especially in methanol. However, the conversion of a solution of I in one of the other above solvents into an aqueous solution of I is also of interest. The preparation of a substantially solvent-free aqueous solution of I from the corresponding solution in an organic solvent by completely removing the solvent by distillation and taking up compound I in water entails large losses in yield because of the unavoidable local overheating and the great sensitivity to heat of compound I (see loc. cit., page 105), and is therefore hardly feasible industrially. If water is first added to a solution of I in an organic solvent and an attempt is then made to distil off the solvent, the solution in general begins to froth so vigorously that conventional distillation is no longer possible. The use of a solvent in which I is less readily soluble, followed by allowing I to crystallize out of the solvent and taking up the compound in water, also does not appear very attractive, because of the large amount of time required, the expensive equipment, and the losses in yield unavoidable in crystallization processes. On the other hand, the reaction cannot be carried out without a solvent, since otherwise (especially when sulfuric acid is used as a proton donor) decomposition of the alcohol, or oxidation of the phosphine to the corresponding phosphine oxide, occurs.

It is an object of the present invention to provide a very simple and economical method of preparing an aqueous solution or fine aqueous dispersion of I.

We have found, surprisingly, that this object is achieved by a very advantageous process for converting a solution, of from about 10 to 70% strength by weight, of a polyenyltriarylphosphonium salt of the general formula I $$[R-P(Ar)_3]^+ X^- \qquad (I)$$

where R is an aliphatic, cycloaliphatic-aliphatic or aromatic-aliphatic polyenyl radical of 5 to 20 carbon atoms, X is the anion equivalent of a strong acid and Ar is aryl, especially phenyl, in an organic solvent, into a substantially solvent-free aqueous solution or fine dispersion of from 10 to 70% strength by weight, wherein the solvent and other steam-volatile compounds originating from the synthesis of I are driven out of the solution, kept at from 30° to 120° C., by means of steam, a part of the steam being allowed to condense in order to produce the aqueous solution. On cooling whilst stirring, such a homogeneous, viscous solution of I is converted to a fine dispersion.

Further, we have found, surprisingly, that this process may be carried out particularly advantageously on a continuous basis by passing the organic solution of I continuously into the top of a column, preferably a packed column, bringing it into contact with steam in counter-current, allowing a part of the steam to condense and taking off the resulting aqueous solution of I continuously from the lower part of the column. The feed of solution of I and of steam can readily be adjusted so that the desired aqueous solution of I can be taken off directly, as the bottom product, in the form of a homogeneous viscous solution.

The hot bottom product is advantageously transferred continuously into a stirred vessel. Cooling and stirring in general converts this hot aqueous solution of I into a dispersion containing finely divided crystalline phosphonium salt dispersed in water or in aqueous phosphonium salt solution.

It is known that the melting points or decomposition points of the triarylphosphonium salts, especially of the triphenylphosphonium bisulfates, are above 100° C. (for example, β-ionylidenetriphenylphosphonium bisulfate melts, with decomposition, at 183°–185° C. whilst axerophthyltriphenylphosphonium bisulfate melts, with decomposition, at 188°–190° C.) and that the solubility of the triarylphosphonium salts in water is low, especially at room temperature. Hence, it was to be expected that on continuous operation in a column, with a decreasing concentration of the organic solvent in the stripping portion of the column, the phosphonium salts would partially crystallize out and choke the column. Surprisingly, however, such difficulties do not arise in the process according to the invention.

The process according to the invention may be carried out batchwise or continuously. Surprisingly, no troublesome foaming occurs in either method.

To carry out the process batchwise, the solution of I in the organic solvent is kept at just below the boiling point of the solvent in a reaction vessel, steam is introduced and the solvent which consequently evaporates, together with other steam-volatile compounds originating from the synthesis of I, and a part of the steam, are allowed to distil from the reaction vessel.

The following remarks are broadly valid for the operating conditions of the continuous method of the invention: the temperature of the solution entering the column should be below the boiling point of the solvent; the column bottom temperature should be about 100° C.; the feed should be regulated so that the solvent substantially evaporates on the packings as the solution passes through the column. For a low feed rate, a short column suffices whilst for high throughputs the column capacity must be correspondingly greater. Details of suitable operating conditions can readily be established by a few preliminary experiments, so that more detailed comments are superfluous. Similar remarks apply to operation under reduced pressure or superatmospheric pressure.

According to the observations we have made hitherto, the good success of the process of the invention is virtually independent of the nature of the polyene radical in the phosphonium salt I. Since the Wittig ylide synthesis in the main serves for the manufacture of compounds of the carotinoid series, especially of vitamin A and its derivatives as well as of β-carotin itself, the polyenyl radicals which are structural units of these carotinoids are of the greatest importance. Phosphonium salts to be mentioned particularly are those where R is α- or β-ionylidene-ethyl (IIa or IIb)

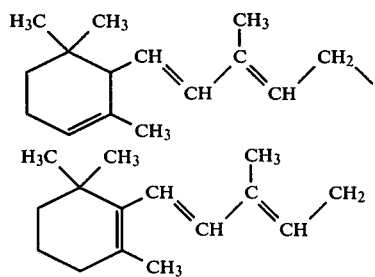

their methyl homologs and the axerophthyl radical (III)

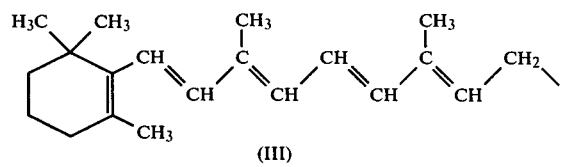

and its methyl homologs. In general, suitable polyenyl radicals are those of 5 to 20 carbon atoms which contain at least 2 conjugated double bonds, of which one can also be a carbon-oxygen bond, as, for example, in the radical

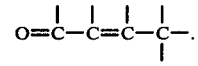

These radicals may also contain further —C≡C— groups and may be substituted by, inter alia, hydroxyl, methoxy or acetoxy. The cycloaliphatic radical can also be replaced by an aromatic radical, eg. phenyl or alkyl-substituted, especially methyl-substituted phenyl.

The nature of the anions in the polyenyltriarylphosphonium salt is also immaterial to the success of the process of the invention. In general, the phosphonium salts of strong acids, eg. $H_2SO_4$, HCl, HBr, HCOOH and $H_3PO_4$ are used, so that X in I is $HSO_4^\ominus$, $Cl^-$, $Br^-$, $HCOO^\ominus$ or $H_2PO_4^\ominus$, preferably $HSO_4^\ominus$.

The process of the invention may in principle be used for converting into an aqueous solution or fine aqueous dispersion a solution of I in any organic solvent which, when steam is blown into the solution, assumes a concentration of 10% or more in the steam leaving the solution, and which boils at from about 50° to 150° C. The process is particularly important for solvents in which polyenyltriarylphosphonium salts can be prepared with particularly good yields, and in which the phosphonium salts are readily soluble. Examples are lower alcohols, eg. methanol, ethanol, n-propanol, iso-propanol, n-butanol and iso-butanol, lower carboxylic acids, eg. HCOOH and acetic acid, acetone and methylene chloride. The process of the invention is used with particular advantage for converting solutions of polyenyltriarylphosphonium salts in methanol.

The solution of I in an organic solvent is prepared in accordance with conventional methods from the triarylphosphine, especially triphenylphosphine, a strong acid, eg, HCl, HBr, HCOOH, $H_3PO_4$ or especially sulfuric acid, and a compound R—X, where X is preferably free hydroxyl or hydroxyl esterified with a lower carboxylic acid, eg. acetic acid. Of course, other methods for the preparation of triarylphosphonium salts may also be used.

Small amounts of triphenylphosphine or of the starting compound R—X, and of by-products formed during this quaternization reaction, are partially volatile in steam so that the process of the invention has the advantage that a pure aqueous solution of I or a pure fine aqueous dispersion is obtained. Since the preparation of a solution of I in an organic solvent forms no part of the present invention, further details thereof are not required here.

The amount and temperature of the required steam depends on specific circumstances. For example, if a solution of I in methanol only is concerned, about 1–3 kg of steam at 100° C. are required to remove 1 kg of methanol. This value decreases with increasing temperature and increases with decreasing temperature and decreasing pressure, so that with a higher steam temperature a more concentrated aqueous solution of I is obtained. If the solution of I in methanol still contains impurities (which as a rule amount to from about 1 to 10 mole% based on I), their removal requires additional steam. From this information, those skilled in the art can determine the optimum process conditions, including the selection of the reflux ratio, by means of a few preliminary experiments. For example, 80–90% strength methanol can be distilled off at the top of the column if the column is suitably designed.

When converting a solution of a polyenyltriarylphosphonium bisulfate in a solvent in which the phosphonium salt is only sparingly soluble, for exammple in iso-propanol or acetone, it is advisable, if the solution of I is to be fed continuously into the reaction vessel, to add a little water to the solution before starting the steam treatment, in order to dissolve phosphonium salt which has crystallized out. In general, it can be said that the presence of a certain amount (up to about 50% by weight) of water in the organic solution of I before or during the steam treatment does not have an adverse effect and in some cases even has an advantageous effect.

If a continuous method is used, the column employed is advantageously a packed column with the appropriate number of theoretical plates for removing the solvent quantitatively. Special aspects of the apparatus or material only arise if the acid aqueous phosphonium salt solution has a corrosive effect on the material of the reaction vessel.

In every case it is possible to remove the solvent completely but in general it suffices to aim at a residual solvent content of from 1 to 2% by weight. The solvent-water mixtures obtained can be separated into their components by distillation, in the conventional manner, and the solvent can be re-used.

The aqueous solution of I or fine dispersion of I in water, obtained as the product, can be used for further reactions, for example for the manufacture of symmetrical carotinoids, eg. β-carotin, or for the manufacture of vitamin A, or can be employed in accordance with conventional methods, for example as a pesticide.

EXAMPLE 1

(a) Preparation of a solution of β-ionylidene-ethyl-triphenylphosphonium bisulfate in methanol 99 g of sulfuric acid and 220 g of 93% pure vinyl-β-ionol were successively added dropwise to a mixture of 700 ml of methanol and 258 g of triphenylphosphine whilst stirring and cooling to 25°–30° C. After 12 hours, the mixture was extracted with 3 times 250 ml of heptane. 1,150 g of a solution, of about 43% strength, of β-ionylidene-ethyl-triphenylphosphonium bisulfate in methanl were obtained.

(b) Conversion of the methanol solution of β-ionylidene-ethyl-triphenylphosphonium bisulfate into an aqueous solution The solution of phosphonium salt in methanol, obtained as described in 1a, was fed, in the course of 90 minutes, into the top of a 50 cm long glass column, of 3 cm diameter, which was packed with glass Raschig rings and insulated. At the bottom of the column, 3,900 g of steam were blown in in the course of the same 90 minutes. The aqueous phosphonium salt solution or suspension was drained off the bottom of the column via a syphon and collected in a stirred flask. About 1,400 g of an easily stirred aqueous suspension, containing 497 g of β-ionylidene-ethyl-triphenylphosphonium bisulfate, were obtained. This corresponds to a yield of 95% of theory.

EXAMPLE 2

(a) Preparation of a solution of axerophthyl-triphenylphosphonium bisulfate in methanol 49 g of sulfuric acid and 164 g of vitamin A acetate were added successively to a mixture of 400 ml of methanol and 131 g of triphenylphosphine in the course of 30 minutes, whilst stirring and cooling to 10° C. The reaction mixture was then stirred for 12 hours at 25° C. 655 g of a solution, of about 38% strength, of axerophthyl-triphenylphosphonium bisulfate in methanol were obtained.

(b) Conversion of the methanol solution of phosphonium salt into an aqueous solution The methanol solution obtained as described in 2a was fed, in the course of 60 minutes, into the top of the packed column described in Example 1. At the bottom of the column, 2,200 g of steam were blown in over the same 60 minutes. About 1,000 g of bottom product were obtained.

(c) Further processing of the aqueous phosphonium salt solution

The resulting aqueous solution of axerophthyl-triphenylphosphonium bisulfate was converted to β-carotene as described in Example 6 of German Laid-Open Application No. 2,505,869. After isomerizing the resulting product in heptane, all-trans-β-carotene was obtained in 70% yield based on vitamin A acetate employed.

EXAMPLE 3

(a) 262 g of triphenylphosphine and 90 g of sulfuric acid were added to 700 ml of glacial acetic acid, whilst stirring. 220 g of 93% pure vinyl-β-ionol were then added dropwise to the reaction mixture in the course of 2 hours, whilst stirring and cooling to ensure that the temperature did not rise above 35° C. Finally, the reaction was allowed to finish in the course of 12 hours, whilst stirring.

(b) The solution of β-ionylidene-ethyl-triphenylphosphonium bisulfate in acetic acid, obtained as described in 3a, was transferred into a flask equipped with a descending condenser and receiver and 1.67 kg of steam were blown into the flask at 30–40 mbar in the course of about 2 hours, during which the temperature rose to 40°–45° C. 1.9 kg of a distillate which essentially contained acetic acid and water, and 1.1 kg of a bottom product, which contained 501 g of β-ionylidene-ethyl-triphenylphosphonium bisulfate as an aqueous solution or suspension, were obtained. The latter corresponds to a yield of 96% based on vinyl-β-ionol employed.

EXAMPLE 4

(a) 258 g of triphenylphosphine and 100 g of crystalline phosphoric acid (dissolved in the minimum amount of water) were added to 700 ml of methanol. 220 g of 93% pure vinyl-β-ionol, corresponding to 0.93 mole, were added dropwise to the above mixture in the course of 2 hours, whilst stirring. The mixture was then refluxed for 1 hour. After cooling, it was extracted with 3 times 250 ml of heptane. 1,150 g of a solution, of about 34% strength, of β-ionylidene-ethyl-triphenylphosphonium phosphate in methanol were obtained.

(b) The methanol solution obtained as described in 4a was treated with steam by the method, and in the column, described in Example 1. 1,400 g of a 26% strength suspension of β-ionylidene-ethyl-triphenylphosphonium phosphate in water were obtained. This corresponds to a yield of 70% based on vinyl-β-ionol employed.

EXAMPLE 5

(a) 262 g of triphenylphosphine were added to 854 g of formic acid whilst stirring. 220 g of 83% pure vinyl-β-ionol were added dropwise to this mixture in the course of 2 hours, whilst ensuring that the temperature of the reaction mixture did not rise above 35° C. The reaction was then allowed to finish in the course of 12 hours, whilst stirring. 1,340 g of a solution, of about 27% strength by weight, of β-ionylidene-ethyl-triphenylphosphonium formate were obtained.

(b) 1.7 kg of steam were blown into the solution obtained as described in 5a, at 40 mbar in the course of 6 hours, using the method and apparatus described in Example 3b. About 1.5 kg of distillate, containing formic acid and water, and 1.5 kg of bottom product, containing 0.65 mole of β-ionylidene-ethyl-triphenylphosphonium formate in solution or suspension in water, were obtained. The latter corresponds to a yield of about 70% of theory, based on vinyl-β-ionol employed.

(c) If the formic acid solution obtained as described in 5a is treated continuously with steam by the method described in Example 1b, virtually the same yield of aqueous β-ionylidene-ethyl-triphenylphosphonium formate is obtained as in 5b.

EXAMPLE 6

(a) 258.5 g of triphenylphosphine were added to 550 g of ethanol and 99.5 g of concentrated sulfuric acid were then added dropwise to this mixture in the course of 15 minutes, followed by 220 g of 95% pure vinyl-β-ionol added dropwise in the course of 60 minutes. The reaction was then allowed to proceed for 20 hours at room temperature. 1,128 g of a solution, of about 40% strength by weight, of β-ionylidene-ethyl-triphenylphosphonium bisulfate in ethanol were obtained.

(b) The solution obtained as described in 6a was treated with steam by the method, and in the column, described in Example 1. 1,400 g of an aqueous suspension containing 454 g of β-ionylidene-ethyl- triphenylphosphonium bisulfate were obtained. This corresponds to a yield of 85% based on vinyl-β-ionol employed.

EXAMPLE 7

(a) 258.8 g of triphenylphosphine were added to 700 ml of isopropanol and 99.5 g of concentrated sulfuric acid were next added dropwise to this mixture in the course of 15 minutes, followed by 220 g of 93% pure vinyl-β-ionol added dropwise in the course of 60 minutes. The resulting β-ionylidene-ethyl-triphenylphosphonium bisulfate partially crystallized out and was dissolved by adding 200 ml of water.

(b) The solution obtained as described in 7a was treated with steam by the method, and in the column, described in Example 1. 1,450 g of an aqueous suspension or emulsion, containing 470 g of β-ionylidene-ethyl-triphenylphosphonium bisulfate, were obtained. This corresponds to a yield of 90% based on vinyl-β-ionol employed.

EXAMPLE 8

(a) 258.5 g of triphenylphosphine were added to 700 ml of isobutanol and 99.5 g of concentrated sulfuric acid were next added dropwise to this mixture, followed by 220 g of 93% pure vinyl-β-ionol, under the conditions described in Example 6. 200 ml of water were then added to the reaction mixture and the batch was heated for 2 hours at 50° C.

(b) The solution obtained as described in 8a was treated with steam by the method, and in the column, described in Example 1. 1,500 g of an aqueous suspension or emulsion, containing 480 g of β-ionylidene-ethyl-triphenylphosphonium bisulfate, were obtained. This corresponds to a yield of 92% based on vinyl-β-ionol employed.

EXAMPLE 9

(a) 258.5 g of triphenylphosphine were added to 700 ml of acetone and 99.5 g of concentrated sulfuric acid were next added dropwise to this mixture, followed by 220 g of vinyl-β-ionol, employing the method described in Example 6. 100 ml of water were then added to the reaction mixture and the batch was heated for 2 hours at 30° C. and then allowed to react for a further 20 hours.

(b) The solution obtained as described in 9a was treated with steam by the method, and in the column, described in Example 1. 1,450 g of an aqueous suspension or emulsion, containing 470 g of β-ionylidene-ethyl-triphenylphosphonium bisulfate, were obtained. This corresponds to a yield of 90% based on vinyl-β-ionol employed.

EXAMPLE 10

(a) 50 ml of pyridine, 50 ml of concentrated aqueous HCl and 6 ml of a 10% strength by weight solution of butylated hydroxyanisole in benzene were added to 700 ml of methanol, the mixture was stirred for 5 minutes, and 139 g of triphenylphosphine and 120 g of 93% pure vinyl-β-ionol were then added as described in German Laid-Open Application DOS No. 2,537,072. The reaction mixture was then extracted with 4 times 250 ml of heptane.

(b) The methanol solution obtained as described in 10a was treated with steam by the method, and in the apparatus, described in Example 1. 1,450 g of an aqueous suspension containing 386 g of β-ionylidene-ethyl-triphenylphosphonium chloride were obtained. This corresponds to a yield of 83% based on vinyl-β-ionol employed.

EXAMPLE 11

262 g of triphenylphosphone were added to 800 ml of methylene chloride. 99.5 g of concentrated sulfuric acid, followed by 220 g of vinyl-β-ionol, were added dropwise at 10°–15° C., whilst stirring and cooling. The solution was then allowed to react for a further 12 hours at room temperature, and was fed continuously, in the course of 90 minutes, into the column described in Example 1, using the method described there.

At the same time, about 2 kg of steam were blown in. 800 ml of methylene chloride and about 1.3 kg of water were obtained as the distillate.

After separating off the water and distilling the methylene chloride, the latter can be re-used.

The bottom product was run out into a stirred flask and cooled to room temperature whilst stirring continuously. 1,200 g of an easily stirred aqueous crystal slurry, containing 497 g of β-ionylidene-triphenylphosphonium bisulfate, were obtained.

This corresponds to a yield of 93% of theory.

We claim:

1. A process for converting an organic solvent solution containing from 10 to 70% strength by weight of a polyenyltriarylphosphonium salt of the formula I $$[R-P(Ar)_3]^+X^- \quad (I)$$

wherein R is an aliphatic, cycloaliphatic-aliphatic or aromatic-aliphatic polyenyl radical of 5 to 20 carbon atoms, X is the anion equivalent of a strong acid, and Ar is aryl to a substantially organic solvent-free aqueous solution or fine dispersion, which comprises:

contacting said organic solvent solution of I with steam to drive out of the solution the solvent while maintaining said solution at a temperature of from 30°–120° C., and condensing a part of the steam to produce the aqueous solution or fine dispersion.

2. The process of claim 1, wherein the organic solvent solution of I is introduced continuously into the top of a column and is brought into contact with a counter-current flow of steam, a part of the steam being allowed to condense and the aqueous solution of I being taken off continuously from the lower part of the column.

3. The process of claim 1 or 2, wherein a solution of I in methanol is used as the starting material.

4. The process of claim 1, wherein the organic solvent solution contains steam-volatile compounds originating from the synthesis of I which are driven out of the solution along with the organic solvent.

* * * * *